United States Patent
Deegan et al.

(10) Patent No.: US 9,095,407 B2
(45) Date of Patent: *Aug. 4, 2015

(54) MAGNETIC INCONTINENCE TREATMENT DEVICE

(71) Applicant: Coloplast A/S, Humlebaek (DK)

(72) Inventors: Christopher Deegan, North Saint Paul, MN (US); Steven McClurg, Brooklyn Park, MN (US); Mark A. Moschel, New Hope, MN (US); Tyler Winsky, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/105,196

(22) Filed: Dec. 13, 2013

(65) Prior Publication Data

US 2014/0100418 A1    Apr. 10, 2014

Related U.S. Application Data

(63) Continuation of application No. 13/217,258, filed on Aug. 25, 2011, now Pat. No. 8,632,451, which is a continuation of application No. 12/868,736, filed on Aug. 26, 2010, now Pat. No. 8,632,450.

(30) Foreign Application Priority Data

Aug. 25, 2010   (DK) .................................. 2010 70371

(51) Int. Cl.
*A61F 2/02*    (2006.01)
*A61F 2/00*    (2006.01)

(52) U.S. Cl.
CPC .............. *A61F 2/0036* (2013.01); *A61F 2/0018* (2013.01); *A61F 2210/009* (2013.01); *A61F 2250/0001* (2013.01)

(58) Field of Classification Search
CPC ...................................................... A61F 2/0036
USPC ..................... 600/9–15, 30, 37; 606/151, 157
See application file for complete search history.

(56) References Cited

U.S. PATENT DOCUMENTS

2003/0144575 A1*   7/2003   Forsell ............................ 600/29

FOREIGN PATENT DOCUMENTS

WO    WO 2008150878 A1 * 12/2008

* cited by examiner

*Primary Examiner* — Jacqueline Cheng
*Assistant Examiner* — Eileen Hyde
(74) *Attorney, Agent, or Firm* — Coloplast Corp.; Nick Baumann

(57) ABSTRACT

An incontinence treatment device includes a band attached to a pendant. The band is implantable around a portion of a urethra and has a first magnet connected to a first end portion of the band and a second magnet connected to a second end portion of the band. The pendant is connected to and extends from the band. The pendant has a shape that configures the pendant to be implantable into a scrotum and a thickness that configures the pendant to be implantable into a labia. The pendant encloses a switch and a power source that are electrically coupled to the first magnet and the second magnet. The switch has an on position to constrict the band around the urethra and an off position in which substantially zero current is provided to decouple the first magnet from the second magnet.

9 Claims, 8 Drawing Sheets

MAGNETIC INCONTINENCE TREATMENT DEVICE

BACKGROUND

Devices for treating urinary incontinence include slings, supports, and other scaffold-like devices that are implanted in a patient's body to support, elevate, or compress the urethra.

A sub-urethral sling is a urinary incontinence treatment device that is surgically implanted under the urethra to support the urethra and inhibit urine from leaking out of the urethra during a provocative event such as coughing or sneezing.

Other urinary incontinence treatment devices, such as injected bulking liquids, are applied to support or partially coaptate the urethra. However, the beneficial effects of an injected bulking liquid can decrease over time.

Improved incontinence treatment methods and devices would be welcomed by both the patient and the surgical staff.

SUMMARY

One aspect provides an incontinence treatment device having a band, magnets, and a power source. The band has a length extending between a first end and a second end. A first magnet is connected to a first end portion of the band and a second magnet is connected to a second end portion of the band. The band is implantable around a urethra and configured to constrict a lumen of the urethra when the first magnet is coupled to the second magnet. The power source is electrically coupled to the first and second magnets and configured to electromagnetically couple and decouple the first magnet relative to the second magnet.

One aspect provides a method of treating urinary incontinence in a patient. The method includes implanting in the patient a device having a band, two magnets, and a power source; placing the band around a urethra; and implanting the power source outside of a pelvis. The power source is operable to electromagnetically couple the two magnets thus constricting a lumen of the urethra.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
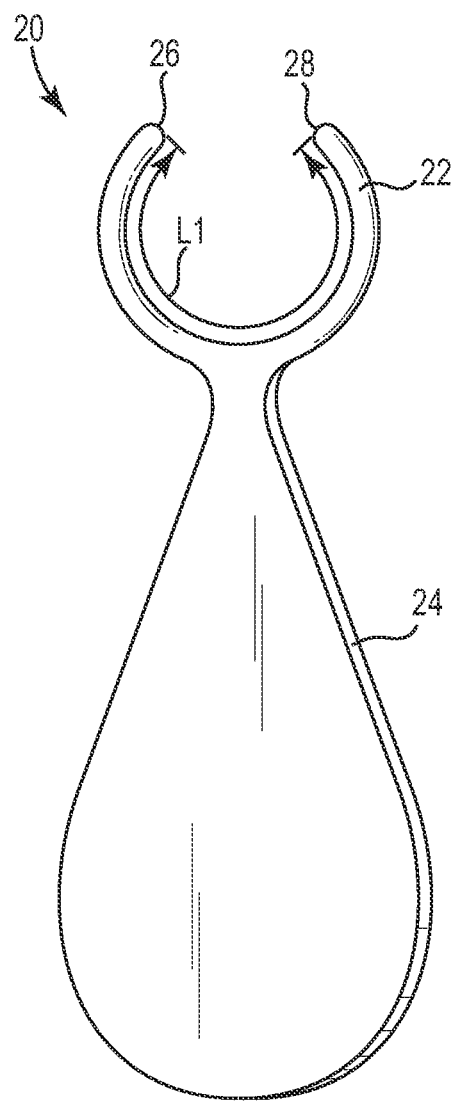
FIG. 1 is a front perspective view of one embodiment of an incontinence treatment device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

A magnet is a material or object that produces a magnetic field. Magnets include permanent magnets that are magnetized and create a persistent magnetic field, and electromagnets formed from a wire that will produce a magnetic field when an electric current passes through the wire. The magnetic field in an electromagnet ceases when the electric current is off. For this reason electromagnets are sometimes called temporary magnets. The strength of a magnet (magnetic moment) and the magnetic field of an electromagnet are proportional to the number of loops (coils) formed in the wire. Wrapping the coils of the wire around a soft ferromagnetic material will produce an electromagnet having a magnetic field strength that is increased by several orders of magnitude.

In this specification, the phrase electromagnetically couple means that the electromagnetic field of one magnet interacts with the electromagnetic field of a second magnet to form an attraction between the magnets. For example, a first magnet having a magnetic field of +H is attracted to a second magnet having a magnetic field of −H such that the two magnets couple together. Magnets that are coupled together can be separated by a distance, with the coupling force provided by the magnetic field extending across the distance. That is, the electromagnets do not need to touch one another in order to couple. Alternatively, the magnets can be coupled together in contact with one another.

In this specification, the term "end" means an end-most extent of an object (such as a band), and the term end portion is that segment of the object that is adjacent to the end.

People suffering from urinary incontinence have a diminished ability to restrict the flow of urine through the urethra, usually due to a damaged or deficient urethral sphincter. The urethral sphincter is a collection of muscles that control the flow of urine from the bladder. These muscles envelop the urethra, and when contracted, seal the urethra shut. In general terms, each person has two urethral sphincters: an internal sphincter muscle of the urethra and an external sphincter muscle of the urethra. The internal sphincter muscle of the urethra is located near the junction of the urethra and the bladder. The external sphincter muscle of the urethra is located at the distal inferior end of the bladder in females and inferior to the prostate (at the level of the membranous urethra) in males.

Hyper-mobile urethras contribute to urinary incontinence in females. A hyper-mobile urethra will translate into alignment with an exit of the bladder, thus creating a "straight-shot" pathway from the bladder that allows urine to escape from the bladder and out of the urethra. Physicians have developed an evaluation to determine if the patient has a hyper-mobile urethra. The evaluation entails the placement of an indicator stick into the longitudinal axis of the urethra such that a portion of the indicator stick extends distally out of the patient's body (those of skill in the art refer to the evaluation as the "Q-tip™ test"). The patient is prompted to initiate a provocative event, for example a cough or a tightening of the abdominal muscles, and the physician observes the indicator stick for movement. Movement of the indicator stick indicates that the longitudinal axis of the urethra is moving, which is indicative of the patient having a hyper-mobile urethra.

The urethra is normally supported by connective and other tissues. Over time, and particularly with parous women, the support of the urethra erodes, giving rise to hyper-mobility of the urethra. Hyper-mobile urethras are susceptible to the undesirable leaking of urine during provocative events such as sneezing, laughing, or coughing (which is sometimes referred to as stress urinary incontinence).

The implant described herein provides the patient with the ability to selectively constrict the urethra, allowing the patient to be continent. The implant includes a band that is selectively constricted around the urethra to close the urethra and thus impede the flow of urine through the urethra. The patient controls the band to select the time and conditions when the urethra is constricted and the time and conditions when the urethra is unconstructed. The implant thus allows the patient to constrict the urethra when golfing, later to open the urethra to urinate, then again operate the implant to constrict the urethra to a selected level for participation in activities, and in the evening, the patient has the ability to remove the constriction to urethra when sleeping when the urge to urinate is decreased.

FIG. 1 is a front perspective view of one embodiment of an incontinence treatment device 20 (device 20) including a band 22 and a pendant 24 extending from the band 22.

The band 22 has a length L1 sized for placement around a urethra, where the length L1 extends between a first end 26 and a second end 28 of the band 22. The human urethra is surrounded by submicosa and muscle and can be depicted as a tubular structure having a nominal diameter of between 1-5 mm. In one embodiment, the length L1 of the band 22 is between about 3-30 mm to encompass at least a portion of an outside diameter of the urethra, and in another embodiment the length L1 of the band 22 is between about 4-11 cm to encompass at least a portion of an outside diameter of the muscle surrounding the urethra. In one embodiment, the band 22 is provided as a flexible tube that encloses a pair of magnets and wiring extending from the magnets.

In one embodiment, the pendant 24 encloses a switch and a power source that is electrically connected to the pair of magnets disposed inside of the band 22. In one embodiment, the pendant 24 is flexible such that the switch is operable through the pendant 24 to activate the power source to cause the pair of magnets to electromagnetically couple and constrict the band 22, as described below. The pendant 24 is sized to be implanted in a human body, for example in the scrotum of a male patient, a labium of a female patient, or subcutaneously, for example in the perineum or inner thigh.

Figure 2:
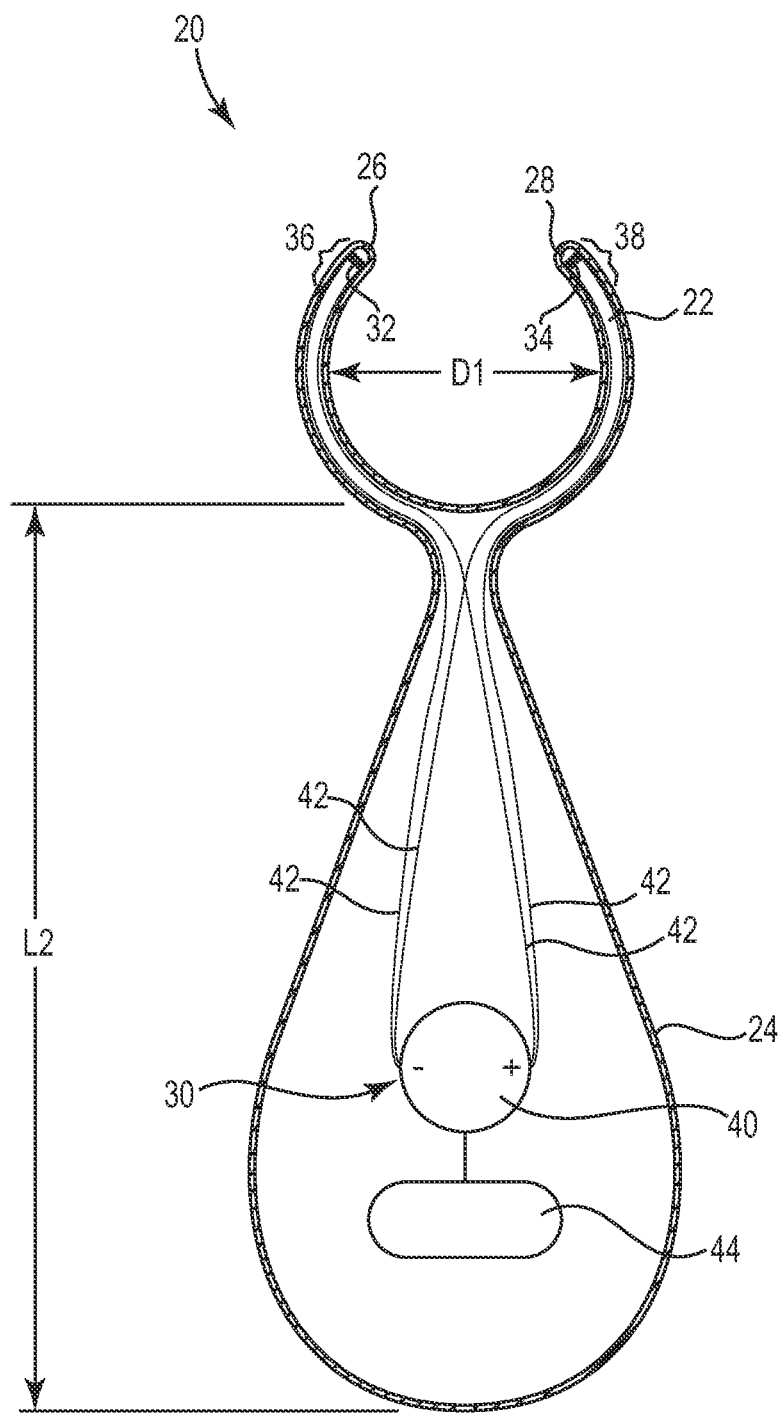
FIG. 2 is a cross-sectional view of the incontinence treatment device illustrated in FIG. 1 showing one embodiment of a pair of opposed magnets connected to a power source.

FIG. 2 is a cross-sectional view of the device 20. In one embodiment, a power source 30 is disposed within the pendant 24 and electrically connected to a first magnet 32 disposed in a first end portion 36 of the band 22 and a second magnet 34 disposed in a second end portion 38 of the band 22. In one embodiment, the power source 30 includes a battery 40 that is electrically connected to the magnets 32, 34 by electrical connectors 42.

It is desirable that the magnets 32, 34 are sealed within the band 22 and that the battery 40, switch 44, and the electrical connectors 42 are sealed within the pendant 24 to protect these components from the effects of moisture. In one embodiment, the components are sealed within the band 22 and the pendant 24, for example by molding a silicone or other material at a suitably low temperature around the components or by fabricating the band 22/pendant 24 around the components in a manner that does not harm the electrical connections/components. The material sealing the components within the band 22/pendant 24 is not illustrated in order to ensure visual clarity for FIG. 2.

The battery 40 provides current to the electrical connectors 42. Suitable batteries include lithium batteries, such as lithium batteries having a lithium-manganese-dioxide batteries (Li—MnO2) cathode and a lithium perchlorate electrolyte, or lithium batteries having a lithium-silver oxide-vanadium pentoxide (Li—Ag2V4O11) cathode and a lithium hexafluorophosphate electrolyte. Other lithium chemistries are also acceptable. In one embodiment, the lithium battery is a nominal 3 volt "coin" battery having a diameter of about 20 mm and a thickness of between 1.6-4 mm.

In one embodiment, each of the magnets 32, 34 is formed from a coiled section of metal wire attached to ends of the electrical connectors 42, and the current from the battery 40 creates a magnetic field in the magnets 32, 34. The direction of magnetic field depends upon the direction that the current is flowing through the electrical connectors 42. The direction of the wiring extending from the battery 40 to the electrical connectors 42 is selected such that the magnets 32, 34 are mutually attractive. For example, the direction of the wiring extending from the battery 40 to the first magnet 32 is wired in the "left-hand" sense and the direction of the wiring extending the battery 40 to the second magnet 34 is wired in the "right hand" sense, such that the magnetic fields produced by the magnets 32, 34 attract each other. To this end, each of the magnets 32, 34 has one electrical connector 42 connected to a positive terminal of the battery 40 and one electrical connector 42 connected to a negative terminal of the battery 40, as illustrated.

In one embodiment, a switch 44 is electrically connected to the power source 30 and is operable to energize the magnets 32, 34 such that the magnets will attract each other and cause the band 22 to constrict, for example around a urethra about which the band 22 is placed. The switch 44 is operable to de-couple the magnets 32, 34 to allow the band 22 to relax and release the constriction applied to the urethra. In one embodiment, the switch 44 has a rebounding button that is clicked once for power on at a first level, two clicks of the button activates the power on at a second level different from the first level, three clicks of the button activates the power on at a third level different from the first level and the second level, and a fourth click of the button turns the power off. In this example, the switch 44 has a cyclic on-off path of off-low-medium-high-off power levels.

The magnets 32, 34 in combination with the power source 30 provide an electromagnet that is operable to selectively constrict and relax the band 22. The magnetic field developed in the magnets 32, 34 is circular and perpendicular to the wire/connectors 42. In one embodiment, each magnet 32, 34 includes a coil of multiple loops the wire/connector 42 wrapped around a ferrous metal bar, such that the magnetic field developed in the magnets 32, 34 is amplified by the windings of the coil. Activating the switch 44 provides current to the magnets 32, 34 which forms an attraction between the magnets 32, 34. The force of attraction between the magnets 32, 34 is controllable as a function of the number of windings in the coil.

In one embodiment, the band 22 is a urethane or silicone tubular housing and provides a nominal diameter D1 of between 1-5 mm and is suitably sized for placement around a urethra. The pendant 24 is implantable the body and has a length L2 between about 2-12 mm and is selected to be implantable in a scrotum of a male patient, a labium of a female patient, or subcutaneously, for example interior the thigh or in the perineum of the patient.

Figure 3:
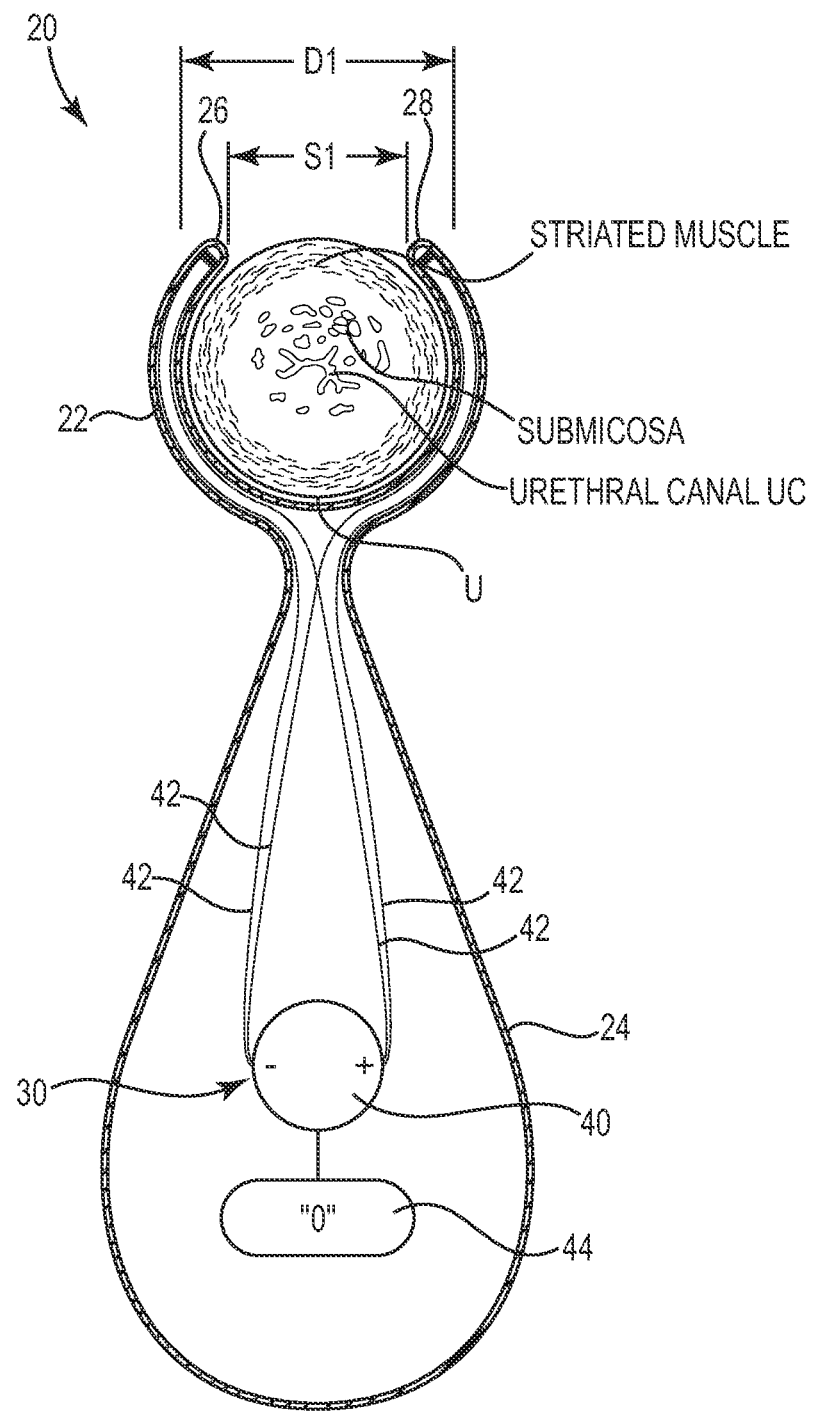
FIG. 3 is a schematic view of the incontinence treatment device illustrated in FIG. 2 implanted relative to a urethra.

FIG. 3 is a schematic view of the device 20 implanted around a urethra U of a patient. The band 22 has the first diameter D1 extending between the interior surfaces of the band 22 and is sized to be placed around a portion of the urethra U. The band 22 is shown in a relaxed, non-constricted state with the first end 26 separated from the second end 28 by a space S1. As illustrated, the switch 44 is in the off position (position "0") such that current is not flowing from the battery 40. The magnets 32, 34 are thus de-coupled (not energized) and the urethra U is not constricted.

The device 20 is implanted, generally, by dissecting down to the bulbous spongiosum located around the urethra U and placing the band 22 at least part-way around the urethra U. The pendant 24 is implanted in a suitable location within the patient, depending upon the gender, in the locations exterior or outside of the pelvis as described above. In one exemplary embodiment, the pendant 24 that encloses the power source 30 is implanted exterior the pelvis in the scrotum of a male patient, or exterior the pelvis in a labium of a female patient.

The urethra U includes a urethral canal UC that is surrounded by tissue. As a point of reference, the lumen of the urethral canal UC is generally not circular, but includes branches (as shown) that expand to allow the discharge of a substantial volume of urine. The urethral canal UC is surrounded by layers of tissue extending radially outward, and include (in order of illustration) submicosa, longitudinal smooth muscle, circular smooth muscle, and striated muscle. The band 22 of the device 20 as placed partway around the urethra U and is operable to provide a patient-initiated first state that constricts the lumen of the urethral canal UC to impede the flow of urine (FIG. 4) and a subsequent patient-initiated second state that relaxes the urethra U to allow the urine to flow through the lumen of the urethral canal UC (FIG. 3).

Figure 4:
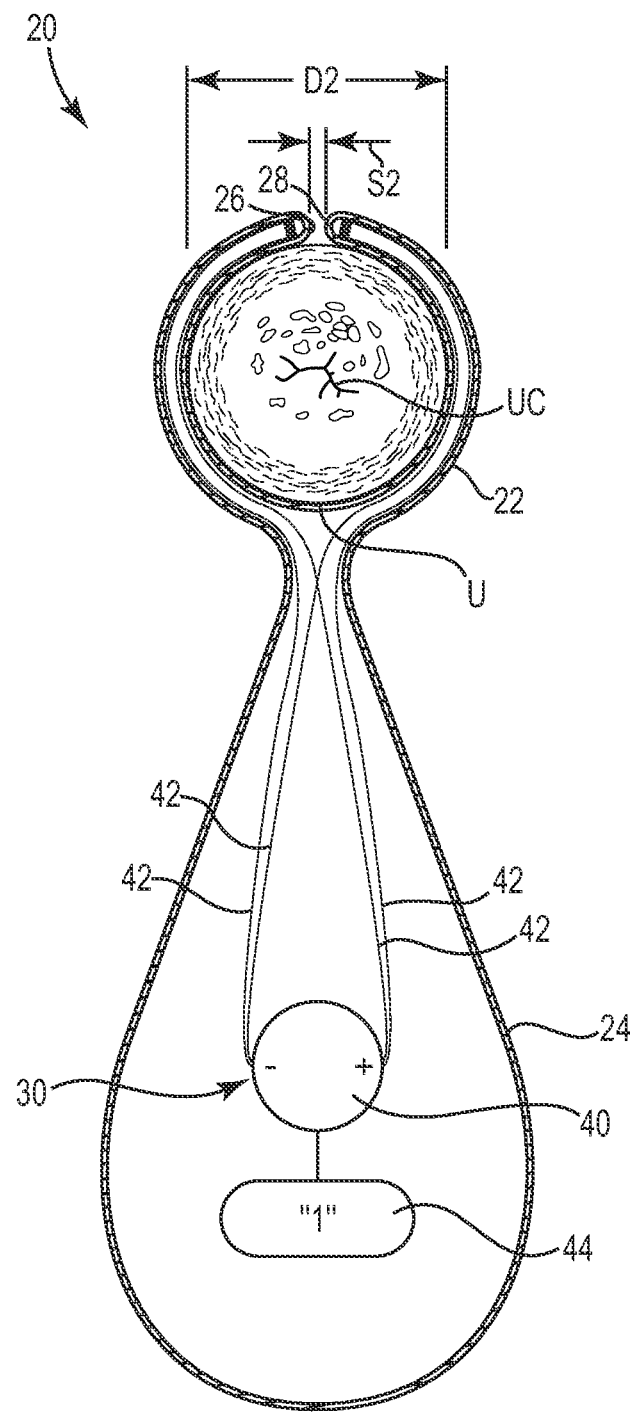
FIG. 4 is a schematic view of the incontinence treatment device illustrated in FIG. 2 activated to constrict a lumen of the urethra.

FIG. 4 is a schematic view of the incontinence treatment device 20 with the switch 44 activated to constrict the lumen of the urethral canal UC. As illustrated, the switch 44 is in an "on" position (position "1") such that current flows from the battery 40 to the magnets 32, 34 (FIG. 2) to couple the magnets 32, 34 and constrict the urethra.

Activation of the switch 44 delivers current to the magnets 32, 34 (FIG. 2) disposed within the band 22. The magnetic field produced in the magnets 32, 34 by the current flowing from the power source 30 causes the magnets 32, 34 to be attracted to one another, which draws the ends 26, 28 of the band 22 together. In one embodiment, the size of the battery 40 and the number of turns or coils provided in the wire of the magnets 32, 34 are selected to provide a magnetic force that pulls the ends 26, 28 of the band 22 together to constrict the diameter of the band 22 from the non-constricted diameter D1 (FIG. 3) down to the constricted diameter D2. In one embodiment, the constricted diameter D2 of the band 22 in the activated state produces a spacing S2 between the ends 26, 28 of the band 22, where the spacing S2 is less than the spacing S1 (FIG. 3) of the band 22 in the decoupled state. The band 22 in the activated state associated with the constricted diameter D2 and the spacing S2 is selected to coapt the lumen in the urethral canal UC to a closed state that prevents the flow of urine through the urethra U.

In general, the switch 44 is provided with an off position (FIG. 3) and at least one on position (FIG. 4). In one embodiment, the device 20 is implanted into the patient and is provided with a default off position in which the lumen of the urethral canal UC is not constricted. In this manner, the urethra U is not constricted if power to the device 20 is interrupted. The patient selectively initiates the device 20 to the on position to selectively coapt the lumen of the urethral canal UC to the closed (continent) position.

Alternatively, the device 20 can be implanted into the patient and provided with a default on position in which the lumen of the urethral canal is constricted to the continent position until the patient selectively switches the device 20 to the off position to open the urethral canal UC.

In one embodiment, the switch 44 is a multi-position switch having multiple "on" positions including a first on position (ON 1) that provides a low amount of constriction to the urethra with a compressive pressure of about 50-60 cm $H_2O$, a second on position (ON 2) that provides a medium amount of constriction to the urethra with a compressive pressure of about 60-70 cm $H_2O$, and a third on position (ON 3) that provides a high amount of constriction to the urethra with an occlusive and compressive pressure of about 70-80 cm $H_2O$. The amount of constriction delivered to the urethra is proportional to the current delivered through the electrical connectors 42 to the magnets 32, 34 and is also proportional to the number of windings in the coils provided to the wire of each of the magnets 32, 34. These variables are determined during the manufacturing of the device 20 to provide the band 22 with a variety of constriction levels as illustrated in Table 1 below. The variety of constriction levels is beneficial to the patient because the patient is empowered to select a low amount of constriction for calm activities such as reading, a medium amount of constriction for activities such as walking, and a high amount of constriction for vigorous or strenuous activities such as golf or tennis. In addition, the patient is able to remove constriction applied by the band 22 to the lumen of the urethra (switch 44 is set to off), which can be desired during the sleeping hours when the urge to void is diminished.

TABLE 1

| Switch Position | Current (mA) | Constriction of Lumen |
| --- | --- | --- |
| OFF | 0 | None |
| ON 1 | + | Low |
| ON 2 | ++ | Medium |
| ON 3 | +++ | High |

With reference to FIGS. 3 and 4, in one embodiment the power source 30 provides means for selectively decreasing constriction applied to the lumen of the urethra U by the band 22. In one embodiment, the power source 30 is connected to the electromagnet 32, 34 and the switch 44 provides means for selectively decreasing constriction applied to the lumen of the urethra U by the band 22.

One embodiment of a method of treating urinary incontinence in a patient includes implanting the device 20 in the patient, placing the band 22 around a portion of the urethra U, and implanting the power source 30 outside of a pelvis of the patient. The power source 30 is operable to electromagnetically couple the two magnets 32, 34 to constrict a lumen of the urethra U. In one embodiment, the band 22 is placed around the urethra in a minimally invasive procedure, preferably through a single incision (although laparoscopic placement is also acceptable), such that the band 22 is implanted in a position around the bulbous spongiosum tissue of the urethra U. The power source is implanted in the patient in a location outside of the pelvis, for example in a scrotum, a labium, or subcutaneously within the patient.

The band 22 applies constriction to the lumen of the urethra U when the magnets 32, 34 are electro-magnetically coupled, and the constriction can be applied at a high force that completely coapts the urethra U for participation in vigorous activity, a medium force that supports and closes the urethra U for participation in moderate levels of activity, a low force that supports and closes the urethra U for participation in low levels of activity, and no force to allow the urethra to relax when the urge to urinate is reduced. In one embodiment, the off position of the switch 44 provides no constriction to the lumen of the urethra, which allows the urethra U to rest or relax, which reduces erosion applied to the urethra from the device 20.

In this manner, the patient is enabled to coapt his/her urinary urethra at a first force for participation in vigorous activity (like golf or tennis), and optionally, selectively adjust the first force to a lower second force to close the urethra for participation in moderate activity (like walking, watching a spectator sport, etc.). During use, the device 20 provides the patient with the ability to constrict the urethra U when active by activating the switch 44 to the on position, selectively open the urethra U to urinate by activating the switch 44 to the off position, selectively activate the switch 44 to one of the multiple on positions to constrict the urethra to a desired level for other activities and/or activity levels, or selectively remove the constriction to urethra U prior to sleeping when the urge to urinate is decreased. In one embodiment, the device 20 is implanted to replace a prostate sphincter removed from a male patient during a prostatectomy such that the device 20 is a prosthetic sphincter.

Figure 5B:
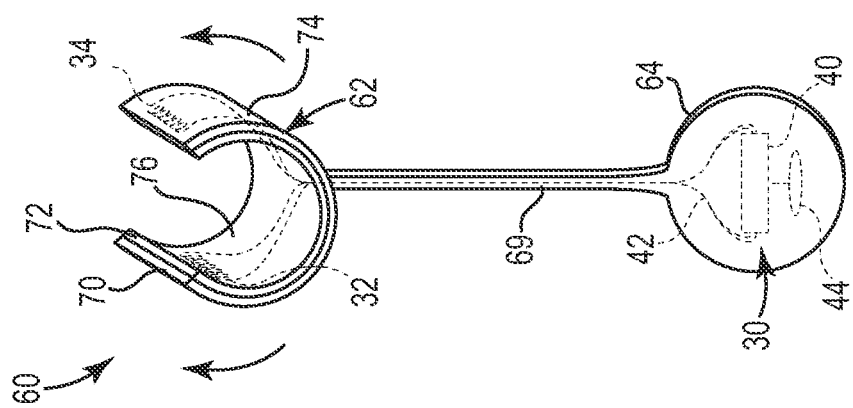
FIG. 5B is a perspective view of the incontinence treatment device illustrated in FIG. 5A configured for implantation around a urethra.
Figure 5A:
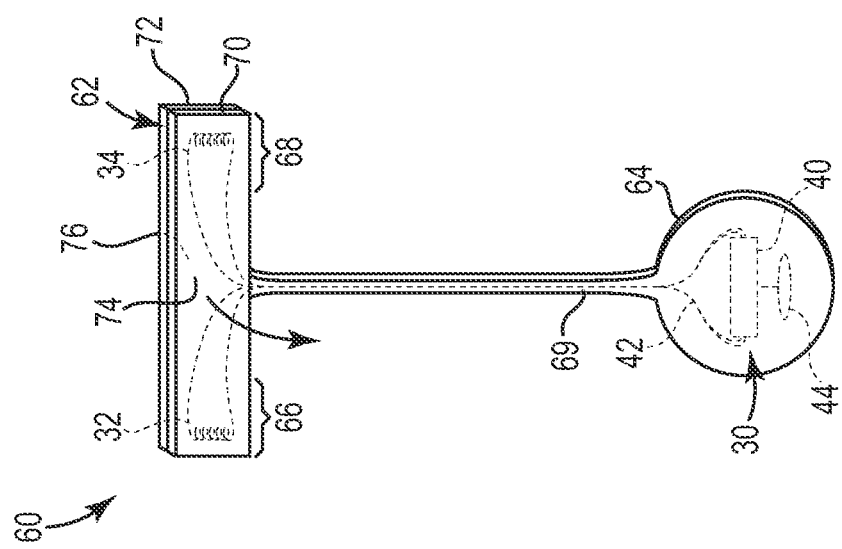
FIG. 5A is a front perspective view of one embodiment of an incontinence treatment device including magnets disposed between layers of a fabric band.

FIG. 5A is a front perspective view of one embodiment of an incontinence treatment device 60 including a band 62 and a pendant 64 extending from the band 62. The pendant 64 is similar to the pendant 24 (FIG. 2) and encloses a power source 30 that includes the battery 40, the switch 44, and the electrical connectors 42 that are electrically connected to the magnets 32, 34. In one embodiment, the first magnet 32 is disposed within a first end portion 66 of the band 62 and a second magnet 34 is disposed within a second end portion 68 of the band 62. In one embodiment, the pendant 64 is provided as a substantially circular pendant having a diameter of between 10-40 mm with a thickness between 2-10 mm. In one embodiment, a sheath 69 is provided that encloses the electrical connectors 42 between the band 62 and the pendant 64. Other shapes and suitable sizes for the pendant 64 are also acceptable.

In one embodiment, the band 62 is provided as a flexible band and includes a first layer 70 and a second layer 72, where the first and second magnets 32, 34 and their associated wiring are disposed between the first and second layers 70, 72. In one embodiment, the band 62 is fabricated of an elastic material, such as an elastic woven fabric. In one embodiment, the band 62 is fabricated of a substantially inelastic material, such as a knitted polyester or nylon fabric. The magnets 32, 34 are enclosed inside of the band 62, which is configured to be suited for implanting around a urethra. In one embodiment, the band 62 is an elongated band having a first major face 74 opposite a second major face 76. The band 62 is suitably fabricated in different formats, including the rectangular format illustrated in FIG. 5A.

In one embodiment, the first and second layers 70, 72 are flexible plastic sheets. Suitable flexible plastic sheets include sheets formed from polyurethane or polyolefin. In one embodiment, the first and second layers 70, 72 are provided as flexible fabric sheets. Suitable flexible fabric sheets include sheets formed from woven fabrics or nonwoven fabrics. One suitable woven fabric for the layers 70, 72 of the band 62 includes a woven nylon fabric. One suitable nonwoven fabric for the layers 70, 72 of the band 62 includes a nonwoven of polyethylene fabric.

FIG. 5B is a front perspective view of the incontinence treatment device 60 in an orientation suitable for implanting around the urethra of the patient. The band 62 has been folded forward such that the second major face 76 is in an "up" position for placement around the bulbous spongiosum tissue of the urethra. The first major face 74 is in a "down" position, with the sheath 69 and the pendant 64 descending from the band 62.

The band 62 is flexible and suited for forming a semicircular arc around a portion of the urethra. When implanted, the band 62 is suitably held in place by the adjacent tissue, although at the surgeon's discretion one or more stabilizing sutures may be placed through the band 62 to anchor it to tissue.

The device 60 is operable similar to the device 20 described above where the power source 30 is electrically connected to the first and second magnets 32, 34 and is configured to electromagnetically couple and decouple the first magnet 32 relative to the second magnet 34 to constrict the band 62 or relax the band 62, respectively. In one embodiment, the switch 44 operates similarly to the modes described above and includes an off position offering no constriction, and high, medium, or low positions that provide increasing amounts of constriction from the band 62 to the urethra about which it is implanted.

Figure 6:
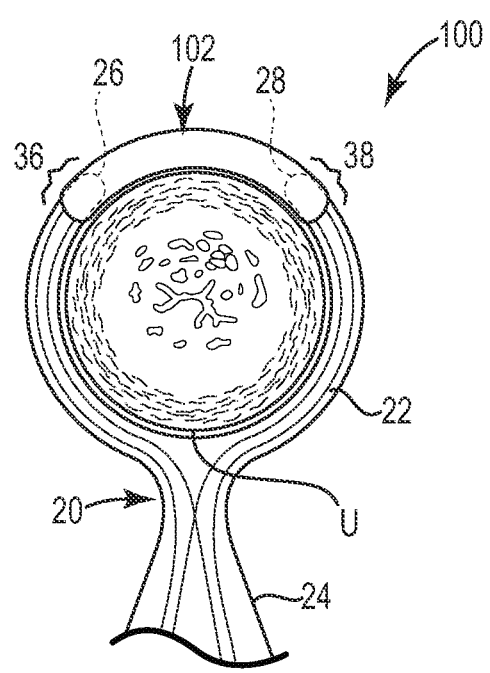
FIG. 6 is a partial front view of one embodiment of a magnetic urinary incontinence assembly including a keeper disposed around a portion of the band of the incontinence treatment device illustrated in FIG. 1.

FIG. 6 is a partial front view of a magnetic urinary incontinence assembly 100 including a keeper 102 disposed around a portion of the band 22 of the incontinence treatment device 20 illustrated in FIG. 1. With reference to FIG. 2, the first magnet 32 is disposed in the first end portion 36 of the band 22 and the second magnet 34 is disposed in a second end portion 38 of the band 22. It is desirable to maintain a relative orientation between the first end 26 and the second end 28 of the band 22 to ensure that the magnets 32, 34 are in position for electromagnetic coupling. In one embodiment, the keeper 102 is provided to maintain the first end portion 36 in alignment with the second end portion 38 to ensure that the magnets 32, 34 are in position for electromagnetic coupling. In one embodiment, the keeper 102 is provided as a tubular sheath (e.g., an open-ended tube sock) that fits over the first end portion 36 and extends to fit over the second end portion 38. The tubular keeper 102 is suitably fabricated from flexible plastic materials, such as plastic sheets or fabrics, or rigid plastic materials.

Figure 7:
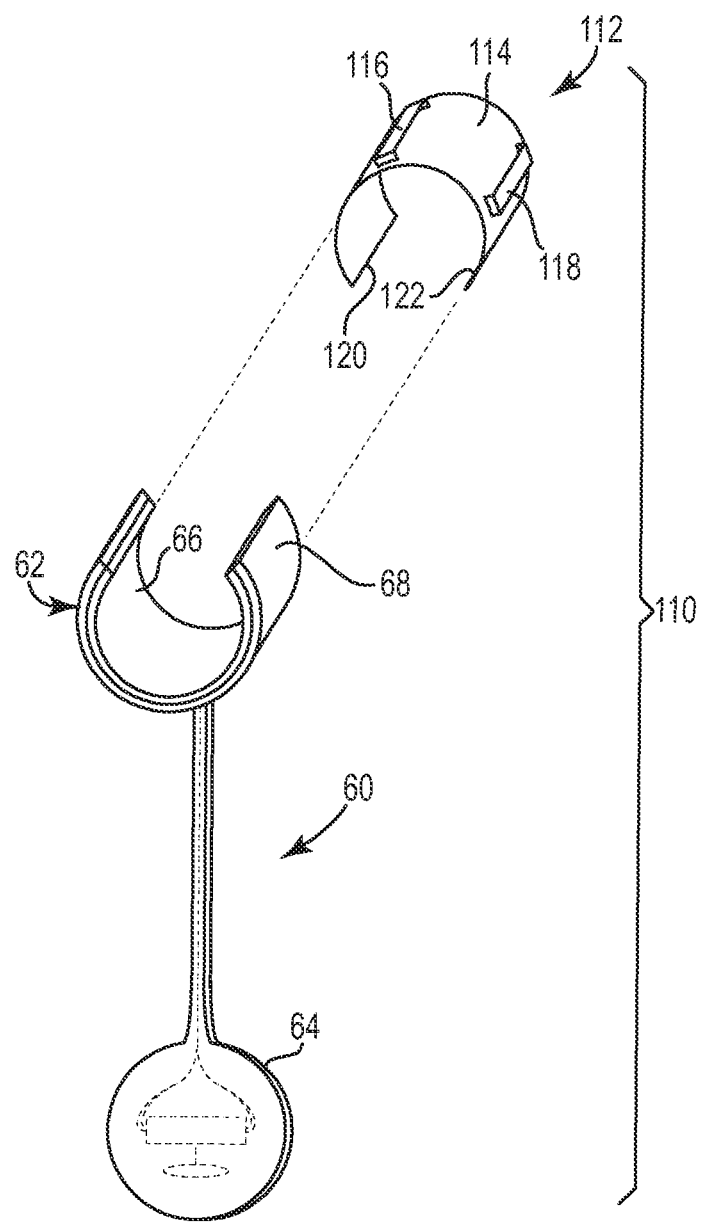
FIG. 7 is a perspective view of one embodiment of a magnetic urinary incontinence assembly including a buckle keeper attachable to a band of the incontinence treatment device illustrated in FIG. 5B.

FIG. 7 is a perspective view of one embodiment of a magnetic urinary incontinence assembly 110 including a buckle keeper 112 attachable to the band 62 of the incontinence treatment device 60 illustrated in FIG. 5B. The buckle keeper 112 includes a base 114 and first and second loops 116, 118 that are disposed between opposed ends 120, 122 of the base 114.

The base 114 is configured to be flexible for implantation around a portion of the external urethra. Suitable material for fabricating the band 114 include plastic sheets, fabric sheets (woven or nonwoven), or rigid molded components. Each of the loops 116, 118 is sized to receive a respective end portion 66, 68 of the band 62. The loops 116, 118 maintain the end portions 66, 68 of the band 62 in alignment, which ensures that the magnets disposed within the band 62 are positioned for electromagnetic coupling when the device 60 is implanted. In one embodiment, the loops 116, 118 are sized to allow the end portions 66, 68 of the band 62 to slide between the loops 116, 118. In one embodiment, one of the end portions 66, 68 or the loops 116, 118 is provided with a stop that prevents the band 62 from being withdrawn or pulled through the loops 116, 118.

Figure 8:
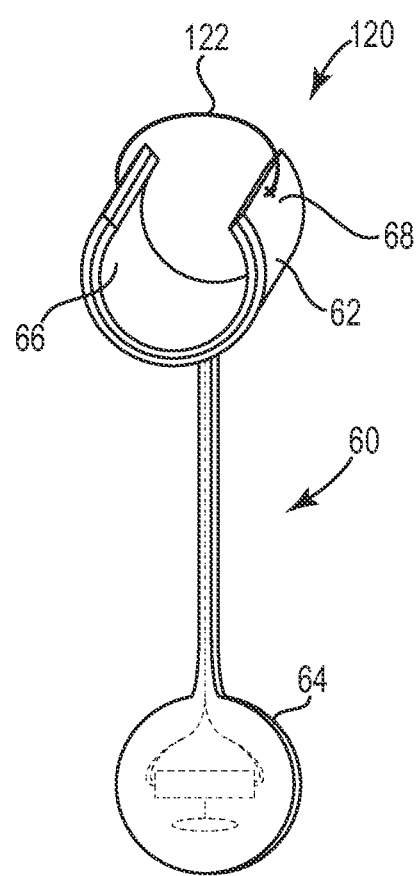
FIG. 8 is a perspective view of one embodiment of a magnetic urinary incontinence assembly including a strand keeper attachable to a band of the incontinence treatment device illustrated in FIG. 5B.

FIG. 8 is a perspective view of one embodiment of a magnetic urinary incontinence assembly 120 including a strand keeper 122 attachable to the band 62 of the incontinence treatment device 60 illustrated in FIG. 5B. In one embodiment, the strand keeper 122 is a suture line that is connected between the first end portion 66 and the second end portion 68 of the band 62 to maintain alignment between the end portions 66, 68. To this end, the end portions 66, 68 are restrained by the keeper 122 in an aligned orientation even when the band 62 is in the relaxed state.

Various incontinence treatment devices are described having an electro-magnetically controlled band that is selectively activated by the patient to close the urethra to provide the patient with continence. The patient controls the band to select the time and conditions when the urethra is constricted and the time and conditions when the urethra is not constructed. For example, the patient may choose to constrict the urethra when golfing, and the patient may choose to remove the constriction to urethra when sleeping when the urge to urinate is decreased.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An incontinence treatment device comprising:
a band implantable around a portion of a urethra, the band having a first magnet connected to a first end portion of the band and a second magnet connected to a second end portion of the band; and
a pendant connected to and extending from the band, the pendant including a first width at a first location where the pendant is connected to the band and a second width at a second location at a mid-portion of the pendant, where the second width of the pendant is larger than the first width such that the pendant is shaped to be implantable into a scrotum, and the pendant has a thickness between opposed major faces of the pendant with the thickness less than the first width such that the pendant is implantable into a labia, the pendant enclosing a switch and a power source that are electrically coupled to the first magnet and the second magnet;
wherein the switch has an on position in which current is provided to couple the first magnet to the second magnet to thus constrict the band around the urethra;
wherein the switch has an off position in which substantially zero current is provided to decouple the first magnet from the second magnet.

2. The incontinence treatment device of claim 1, wherein the switch operates to select a range of power levels including a low power level, a medium power level and a high power level.

3. The incontinence treatment device of claim 1, wherein the switch is a multi-position switch having multiple on positions including a first on position that provides a first current to the first and second magnets and a second on position that provides a second current to the first and second magnets that is greater than the first current.

4. The incontinence treatment device of claim 1, wherein the switch is a cyclic switch providing an on-off path including an off power level, a low power level, a medium power level, a high power level, and a return off power level that allows the power source to electromagnetically couple and decouple the first magnet relative to the second magnet.

5. The incontinence treatment device of claim 1, wherein the first magnet and the second magnet each comprise a coiled metal wire and the power source comprises a battery connected to the switch;
wherein the switch is operable to allow current to flow from the battery to the coiled metal wires.

6. The incontinence treatment device of claim 1, wherein the pendant is tear drop shaped.

7. An incontinence treatment device comprising:
a band implantable around a portion of a urethra, the band having a first magnet connected to a first end portion of the band and a second magnet connected to a second end portion of the band;
a pendant connected to and extending from the band, the pendant including a first width at a first location where the pendant is connected to the band and a second width at a second location at a mid-portion of the pendant, where the second width of the pendant is larger than the first width such that the pendant is shaped to be implantable into a scrotum, and the pendant has a thickness between opposed major faces of the pendant with the thickness less than the first width such that the pendant is implantable into a labia, with the pendant enclosing a switch that is electrically coupled to the first magnet and the second magnet; and
means for selectively decreasing constriction applied to the urethra by the band;
wherein the switch has an on position in which current is provided to couple the first magnet to the second magnet to thus selectively constrict the band around the urethra.

8. The incontinence treatment device of claim 7, wherein the switch is a multi-position switch having multiple on positions including a first on position that provides a first current to the first and second magnets and a second on position that provides a second current to the first and second magnets that is greater than the first current.

9. The incontinence treatment device of claim 7, wherein the switch has an off position in which substantially zero current is provided to the first magnet and to the second magnet to thus remove constriction applied to the urethra by the band.

* * * * *